United States Patent [19]

Dilworth

[11] Plant 4,825

[45] Feb. 16, 1982

[54] YELLOW KALANCHOE PLANT

[75] Inventor: William L. Dilworth, Amarillo, Tex.

[73] Assignee: J & L Plants Inc., Amarillo, Tex.

[21] Appl. No.: 171,022

[22] Filed: Jul. 22, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Frank B. Robb

[57] ABSTRACT

A kalanchoe plant having the charcteristics of both a yellow color and a distinct lemon fragrance which is not known in other yellow kalanchoes, together with a tall growth habit of approximately 12 to 16 inches, the profusion of flowers on sturdy stems, with the further aspect of adaptability to year round flowering effected by photo period control, the flower color and form being maintained for relatively long periods of time even though growth takes place in a relative dark home environment.

1 Drawing Figure

The present invention relates to a new and distinct variety of kalanchoe plant which was discovered by me as a self-pollinated seedling of the variety Rachel, U.S. Plant Pat. No. 3,821.

The fact that the seedling of yellow color was growing in a large group of the Kalanchoe Rachel, which is a very distinct color in fact cinnamon in color, made the instant seedling stand out and attracted my consideration.

Upon studying the seedling I found that it had the desirable lemon fragrance which is preferably associated with the color yellow and thus made it a logical selection, particularly when other characteristics, of the plant were discovered to comprise the following combination of unique aspects and principal elements which are outstanding:

(1) The upright vigorous growth;

(2) Its tall habit, 12 to 16 inches as compared with "Rachel" which is somewhat shorter being 10 to 12 inches in height;

(3) A profusion of flowers on sturdy stems;

(4) The unique yellow color of blooms emphasized by the profuse quantity and lemon fragrance which is not known in other yellow kalanchoe;

(5) The adaptability to year round flowering by photo period control which is desired in plants and particularly in kalanchoes;

(6) Being a short day plant it flowers naturally around the middle of December, a blooming period of 4 to 5 weeks, likewise desired in kalanchoe plants.

Particular novel and distinctive aspects of the kalanchoe variety of my discovery herein, are described and apparent from the detailed description set forth in the following.

I have caused the plant to be asexually reproduced by cuttings, performed in a greenhouse to which I have access located at Canyon, Tex., and such reproduction confirms my statement that the foregoing characteristics and distinctions come true and are established and transmitted through succeeding propagations.

The accompanying drawing shows a typical view of a plant of my new variety, as depicted in color as nearly true as it is possible to effect such reproduction in a color illustration of this character.

The following is a detailed description of my new kalanchoe variety, with color terminology selected from Munsell Color Cascade, which is produced by the Macbeth Division of Kollmorgen Corporation, except where general color terms of ordinary dictionary significance are applicable and appropriate the observations referred to having been made in natural light:

Parentage: Seedling. Self-pollinated seedling of Rachel, U.S. Plant Pat. No. 3821.

Propagation: Holds its distinguishing characteristics through succeeding propagations by rooting of stem cuttings.

Locality where grown and observed: Canyon, Tex.

Plant:

*Form.*—Much-branched; upright; growing to a height of 12 to 16 inches.

*Growth habit.*—Medium vigor; branching.

*Rooting habit.*—Roots easily from a part of the stem, forming a fibrous root system.

*Blooming habit.*—As a short day plant, flowers naturally around the middle of December.

*Blooming season.*—With the technique of photo period control the variety may be caused to flower the year around.

Foliage:

*Size.*—Large.

*Quantity.*—Abundant.

*Color.*—New foliage — Upper side — 21-14. Under side — 21-13. Old foliage — Upper side — 21-13. Under side — 21-13. Shape — Obtuse. Texture — Upper side — Glossy; smooth. Under side — Smooth. Edge of margin — Shape — Oval. Aspect — Entire.

Disease resistance: Compares very favorably to other new varieties being superior to old standard varieties as being compared to other varieties grown in comparable greenhouse conditions, at Canyon, Tex.

Flowers: Pistillate; staminate.

*Size.*—Flower diameter 18 mm. Flower depth 16 mm. Petal width 8 mm. Petal length 9 mm.

*Form.*—Umbel.

*Color.*—Petals. Upper side — 27-4. Lower side — 27-2.

*Blooming period.*—4 to 5 weeks.

Hardiness: When grown in greenhouse at temperatures from 50° F. to 100° F. no apparent problems have been observed.

General observations: Has all the quantities for good potted plants, and since lemon fragrance is very often associated with a yellow color, my new variety is particularly attractive. This is especially appealing because heretofore known yellow kalanchoe plants have not produced such fragrance. The excellent keeping qualities and abundant flowers, make the same valuable as a house plant especially since the blooms last 4 to 5 weeks even in relatively dark home conditions adding to its value as a commercial variety.

I claim:

1. A new and distinct variety of kalanchoe plant, substantially as herein shown and described, characterized particularly as to novelty by the unique combination of the lemon fragrance with a yellow color, a tall habit of growth, its later flowering period, its response to photo period manipulation to produce flowers on a year around basis, good keeping, long lastingness in relatively dark environment, profusion of blooms on sturdy stems.

* * * * *

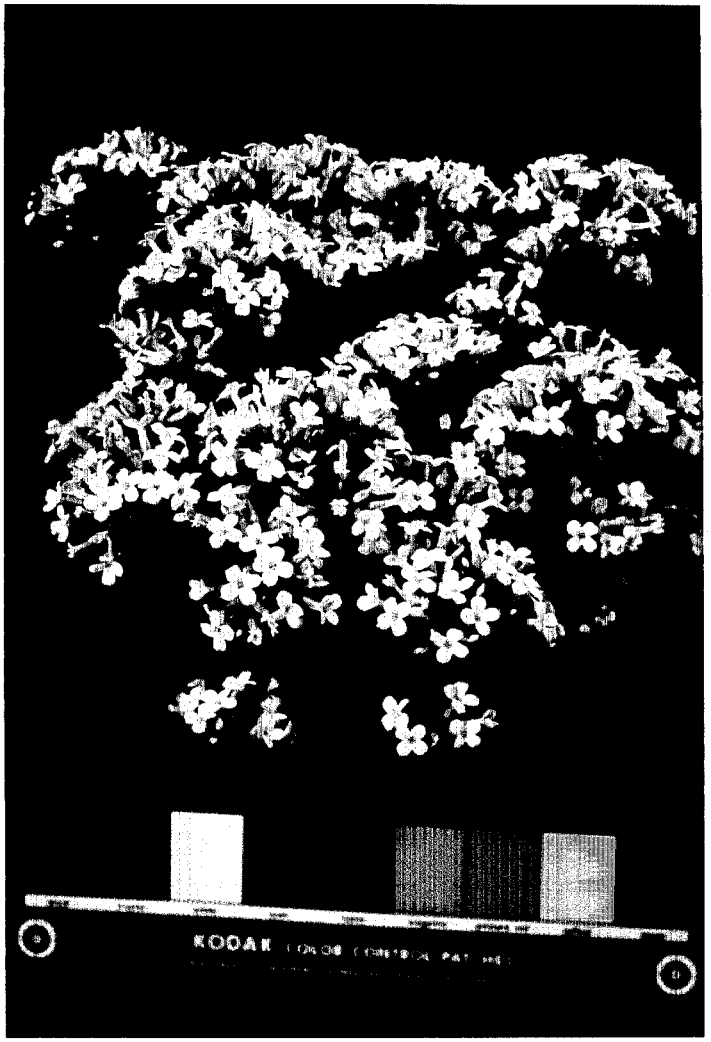
KODAK